United States Patent [19]

Pao et al.

[11] Patent Number: 5,544,208
[45] Date of Patent: Aug. 6, 1996

[54] METHOD AND APPARATUS FOR IN SITU DETECTION OF DEFECTIVE NUCLEAR FUEL ASSEMBLY

[75] Inventors: Hsueh-Wen Pao, Saratoga; David L. Faulstich, San Jose; Dane T. Snyder, Byron; Johnny T. Ma, San Jose; Kenneth R. Izzo, Los Gatos; Joel C. Swanson, Livermore; Martin S. Laurent, San Jose; Peter F. Kachel, Livermore, all of Calif.

[73] Assignee: General Electric Company, San Jose, Calif.

[21] Appl. No.: 309,383

[22] Filed: Sep. 20, 1994

Related U.S. Application Data

[63] Continuation-in-part of Ser. No. 228,526, Apr. 15, 1994.

[51] Int. Cl.$^6$ .................................................. G21C 17/00
[52] U.S. Cl. .......................... 376/253; 376/250; 376/251
[58] Field of Search ..................................... 376/253, 250, 376/251, 245; 976/DIG. 227, DIG. 209

[56] References Cited

U.S. PATENT DOCUMENTS

| | | | |
|---|---|---|---|
| 3,523,868 | 8/1970 | Dady | 376/253 |
| 3,617,709 | 11/1971 | Tone | 250/83.6 |
| 3,663,363 | 5/1972 | Crouthamel et al. | 376/251 |
| 3,680,284 | 8/1972 | Schmeling | 55/208 |
| 3,775,245 | 11/1973 | Delisle et al. | 376/253 |
| 3,878,040 | 4/1975 | Martucci | 376/253 |
| 3,963,460 | 6/1976 | Stumpf et al. | 55/66 |
| 3,993,542 | 11/1976 | Blum et al. | 376/311 |
| 4,016,749 | 4/1977 | Wachter | 73/45.5 |
| 4,034,599 | 7/1977 | Osborne et al. | 73/40.7 |
| 4,038,060 | 7/1977 | Kamiya et al. | 62/36 |
| 4,039,376 | 8/1977 | Wachter | 376/252 |
| 4,135,970 | 1/1979 | Mitsutsuka et al. | 376/253 |
| 4,147,587 | 4/1979 | Utamura et al. | 176/19 LD |
| 4,226,675 | 10/1980 | Lewis et al. | 376/256 |
| 4,299,661 | 11/1981 | Campana | 376/251 |
| 4,369,048 | 1/1983 | Pence | 55/66 |
| 4,415,524 | 11/1983 | Gross et al. | 376/216 |
| 4,435,644 | 3/1984 | Heki | 250/435 |
| 4,447,353 | 5/1984 | Pence et al. | 252/630 |
| 4,650,637 | 3/1987 | Chubb | 376/253 |
| 5,235,624 | 8/1993 | Bordy et al. | 376/253 |
| 5,414,742 | 5/1995 | Hornak et al. | 376/251 |

FOREIGN PATENT DOCUMENTS

| | | |
|---|---|---|
| 0019303 | 11/1980 | European Pat. Off. . |
| 2272467 | 12/1975 | France . |
| 2315148 | 1/1977 | France . |
| 234102 | 3/1986 | Germany . |
| 898219 | 6/1992 | United Kingdom . |

*Primary Examiner*—Donald P. Walsh
*Assistant Examiner*—Meena Chelliah
*Attorney, Agent, or Firm*—James E. McGinness

[57] ABSTRACT

A process and a system for detecting defective nuclear fuel assemblies in situ. The system includes two basic subsystems. The first subsystem is a sample collection system consisting of a hood placed over the fuel. A technique whereby a vacuum is drawn across a submerged nozzle of a degas tank is used to draw up the sample of fluid out of a fuel assembly. The second subsystem determines the amount of Kr-85 radioisotope contained in the fluid sample. This information is used to determine whether the fuel assembly contains a defective, i.e., leaking, fuel rod. The measurement values for Kr-85 in the fluid sample extracted from the fuel assembly are compared to the measurement values for Kr-85 in fluid samples taken from the reactor pool prior to fuel assembly testing and fluid samples taken from non-leaking control cells, the latter values representing the background to which the subject fuel assembly is compared. Based on this comparison, a determination is made concerning whether the subject fuel assembly is defective.

20 Claims, 4 Drawing Sheets

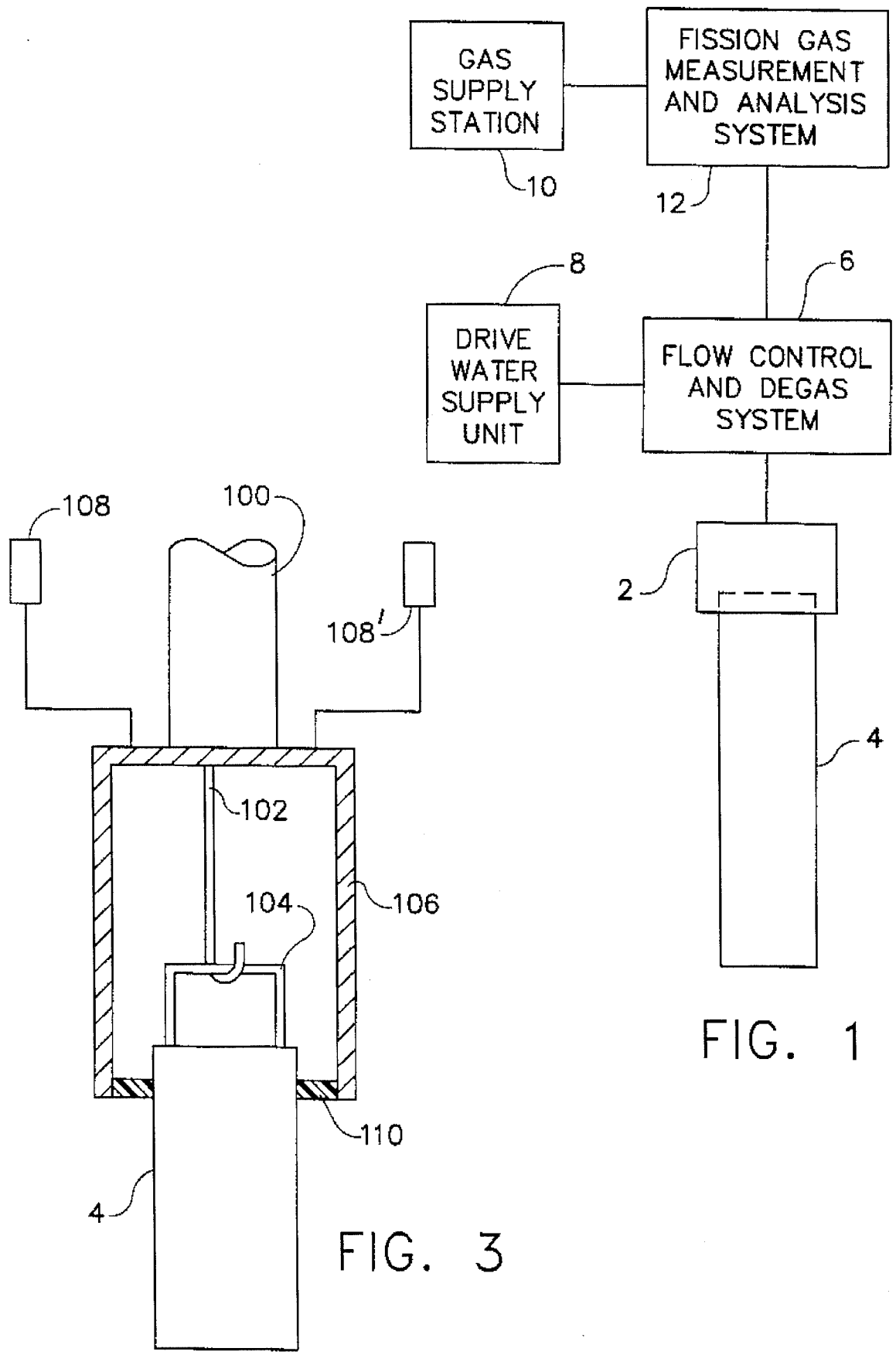

METHOD AND APPARATUS FOR IN SITU DETECTION OF DEFECTIVE NUCLEAR FUEL ASSEMBLY

RELATED PATENT APPLICATIONS

This application is a continuation-in-part application of U.S. patent application Ser. No. 08/228,526 filed on Apr. 15, 1994, now allowed.

FIELD OF THE INVENTION

This invention relates to a method and an apparatus for identifying defective fuel elements that are used in the core of a water-moderated nuclear reactor.

BACKGROUND OF THE INVENTION

The core of a nuclear reactor comprises a plurality of nuclear fuel assemblies, each assembly consisting of a plurality of nuclear fuel rods. Each fuel rod comprises a circular cylindrical housing, i.e., cladding, which is sealed at both ends by respective end plugs. A plurality of nuclear fuel pellets are stacked in a vertical column inside the cladding to a height less than the length of the cladding, leaving a plenum space above the fuel column. A compression spring is placed inside the plenum for biasing the fuel pellets toward the bottom end plug of the fuel rod. A getter for removing contaminants from the interior atmosphere is conventionally installed inside the plenum.

The cladding serves two primary purposes: first, the cladding prevents contact and chemical reaction between the nuclear fuel and the coolant/moderator; and second, the cladding prevents the radioactive fission products, some of which are gases, from being released from the fuel rod into the coolant/moderator. Failure of the cladding, due to build-up of gas pressure or any other reason, could result in contamination of the coolant/moderator and associated systems by radioactive long-lived products to a degree which would interfere with plant operation.

A conventional technique for identifying defective fuel elements in water-moderated nuclear reactors is known as "fuel sipping". This technique identifies leaking fuel rods by obtaining and measuring fission gases that leak out of defective fuel rods. A known method and apparatus for performing fuel sipping is disclosed in U.S. Pat. No. 4,034,599, assigned to the present assignee, the disclosure of which is incorporated by reference herein. In accordance with this conventional technique, fuel sipping is accomplished by isolating a fuel assembly in a test chamber of purified water. The test chamber may be located either in the reactor vessel or at the bottom of the fuel pool. A fuel assembly or a fuel rod is removed from the core or fuel storage rack and placed in a closed container, the background is diminished, and a gas sample which is released from the fuel assembly or rod is obtained from the sipping container. The test chamber contains an exhaust line near the top and a gas sparger at the bottom. Air is introduced into the test chamber through the gas sparger and is allowed to displace a portion of the water above the fuel element. This serves to form an air pocket above the fuel element, reduce the pressure in the test chamber and simultaneously purge the water surrounding the fuel element of fission gases pulled from defective fuel elements. The activity of fission gases entrained in the air are then measured by passing the air through a suitable radiation monitor. In a second step in the method, the pressure in the test chamber is further reduced to a vacuum, so as to increase the release of fission gases. In a third step of the method, the pressure in the test chamber is held at a vacuum and gas drawn from the air pocket above the fuel element for testing is recirculated so as to continuously purge released fission gases from the water surrounding the fuel element. In this manner, purge air and fission gas are trapped in the air pocket in the top of the test chamber and are removed for monitoring via a sample line. The radiation monitor in accordance with U.S. Pat. No. 4,034,599 is a gross beta detector. This detector simultaneously responds to both Kr-85 and Xe-133, which are the major fraction of the fission gases. This system is very accurate, but slow in determining if a slow leaker is present, due to the need to remove the fuel elements from the reactor and due to the time-consuming nature of the detection process.

The measurement of fission gases is a key element of the fuel sipping process because of the easily achieved separation of gas and water. However, the Xe-133 isotope is a decay product of I-133, which is a water-soluble ion. In the case of the aforementioned vacuum sipper, this results in a background problem which is minimized by using demineralized make-up water. Demineralized condensate cannot be used because it often causes problems due to the release of Xe-133 from the decay of I-133 which has been carried over in the steam and exchanged on the condensate demineralizers. Pool water has large quantities of I-133 uniformly distributed therein. The concentration of I-133 is greatly increased when fuel pellet material escapes through a defect in the fuel rod cladding. These background problems must be considered when a slow leaker is observed. In this case, a small increase in fission gas is indicated during the gas recirculation mode of a fuel sip using the vacuum sipper. This increase could be due to a very small defect in a rod, pool water leaking into the test chamber, or desorption of gas from the oxide film which may also contain I-133 (chemically bound). This is a problem because it can lead to false identifications of a leaking fuel rod.

The Kr-85 isotope should not present this type of background problem because there are no water-soluble ionic species in its decay scheme. Therefore, once any species migrates from the inside to the outside of the fuel rod, it will separate and be swept away. It should be noted that Kr-85 is not nearly as abundant as Xe-133. The only technique used to determine the quantity of Kr-85 in the presence of Xe-133 is to make repeated measurements of a specific sample over a long period to determine the decay characteristics of the mixture and calculate the respective quantities of Kr-85 and Xe-133 based on the decay half-lives. This measurement procedure can take months to complete. The rapid measurement of Kr-85 (exclusively) reduces or eliminates a false positive response in the fuel sipping process.

SUMMARY OF THE INVENTION

The present invention is a process for in situ detection of defective fuel. The goal of this process is to find (collect, separate, and identify) trace releases of Kr-85 in the fuel assembly produced by slow leakers in the ambient environment in the nuclear fuel core.

The system of the invention comprises two basic subsystems. The first subsystem is a sample collection system consisting of a hood placed over the fuel. A novel technique is used to draw up the sample of fluid out of a fuel assembly or, alternatively, a fuel cell comprising a square array of four fuel assemblies. The second subsystem is a system for determining the amount of Kr-85 radioisotope contained in the fluid sample. This information is used to determine whether the fuel assembly contains a defective, i.e., leaking, fuel rod. The measurement values for Kr-85 in the fluid sample extracted from the fuel assembly are: (1) compared to the measurement values for Kr-85 in fluid samples taken from the reactor pool prior to fuel assembly testing, and (2) the measurement values for Kr-85 in fluid samples taken from a control cell which has been determined to not contain a leaker, the latter values representing the background to which the subject fuel assembly is compared. Based on this comparison, a determination is made concerning whether the subject fuel assembly is defective.

The sample collection subsystem in accordance with the present invention will, depending on the specific application, incorporate one of four different hoods: a four-head hood, a two-head hood, a single-head hood and a mast-mounted hood. The four-head hood is configured to cover one fuel cell comprising a 2×2 array of fuel assemblies. One or more of these four-head hoods may be used in a sipping campaign to check an entire fuel core. The two-head and single-head hoods are used for core areas which cannot be reached by the four-head hood. The mast-mounted hood is mounted on the refueling mast. The goal is to seal as close as possible to the fuel assembly or cell to enable fluid (i.e., water and gas) to be drawn from each fuel assembly or cell without cross-contamination from adjacent fuel assemblies or cells or from surrounding water inside the reactor pressure vessel.

Several methods can be utilized to cause the fuel assembly and contained water to release the gas sample. Initially the fuel assembly is covered with the hood such that flow is blocked or controlled to allow the fuel assembly to heat up from the residual decay heat. Assuming standard pressure-volume-temperature conditions, increases in gas temperature inside the rod should result in increases in gas volume as long as the gas is contained in the rod (a broken or cracked end cap may allow the gas to escape). This may encourage any gas trapped inside a fuel rod to increase in volume and find its way out.

The water internal to the fuel assembly will then be quickly brought up and sparged into the degas tank for vacuum degassing. Momentarily, this rapid relocation of the water may also increase a locally small pressure difference between the fuel assembly water and the rod internal pressure to help assist in bubble release.

For the on-mast head collector, greater reliance is placed on the ability to trap gas given off by the fuel assemblies as they are raised towards the surface. In this case the water pressure decreases due to the mast elevation changes, creating a pressure differential between the inside of the rod (high) and the outside environment (low). The gas will be trapped by the mast-mounted hood. Then the assembly may be subjected to the pressure transient process to assist in gas release.

For all types of sipping hoods, as the vacuum degassing process begins, an initial sample is shuttled through a beta detector under high pressure. The beta detector's sample chamber is a bolted pressure-tight hemisphere. The hemispherical chamber geometry and pressurized samples maintain the detector efficiency as high as possible, and the bolted construction permits easy access to the sample chamber for decontamination. If an immediate signal is obtained above a certain level, it can be determined the fuel assembly is a leaker. The sample is then disposed of and the next fuel assembly is sampled.

Samples which do not show a gross leaker are sent through a moisture/separation column containing two packings: a first packing which absorbs moisture and a second packing which absorbs xenon gas but passes krypton gas. A sample of the xenon-free gas output from the separation column is then accumulated in an ampoule for subsequent transmission to the beta detector. Since xenon has been removed from the sample, any beta activity detected as the pressurized gas sample passes through the beta detector indicates the presence of krypton. Beta activity at a level in excess of the background level indicates a leaking fuel rod in the tested fuel assembly.

In accordance with the present invention, a programmable logic controller is used to control pumps, valves, timers, etc. To improve efficiency, four detection channels can be connected in parallel between the beta detector and one or more sipping hoods. The gas flow through the channels is remotely and electrically controlled via a plurality of solenoid-actuated valves. Each channel consists of a degas tank, a moisture/separation column and a gas sample ampoule connected in series. Each degas tank is alternatingly connectable to a corresponding head of either of two four-head hoods mounted on respective 2×2 array of fuel assemblies. In accordance with a multiplexing sequence, each detection channel operates concurrently but out of phase with respect to each other. In this way gas samples can be obtained from eight fuel assemblies during each detection cycle by multiplexing the eight gas samples through the four separation channels to a single detector. The programmable logic controller can be programmed as required to remotely control a plurality of solenoid-actuated valves in accordance with the desired multiplexing sequence.

The invention incorporates a process and system for the rapid separation and measurement of Kr-85. By measuring the amount of Kr-85 radioisotope which is present, false positive signals for the vacuum sipping process can be eliminated. The invention utilizes a column to separate the radioisotopes to improve the resolution of spectrum analysis with low-resolution detectors. The general detection process in accordance with the invention is as follows: (1) Moisture is removed from the fission gas stream. (2) The xenon gas is trapped by passing the gas stream through an adsorbing media. (3) The discharge from the adsorbing media is diverted to an evacuated ampoule and momentarily held prior to being directed to the beta detector. Any minute amount of Kr-85 flows through the beta detector, free of Xe133. The quantity of Kr-85 is the prime measurement because it must come from a defective rod within the tested fuel assembly, in accordance with the decay scheme of the fission gas constituents.

BRIEF DESCRIPTION OF THE DRAWING

FIG. 1 is a block diagram showing a gas sipping system for in situ detection of a leak in a fuel assembly in accordance with one preferred embodiment of the present invention.

FIG. 3 is a schematic diagram showing a gas sipping hood (sectioned) mounted on a refueling mast in accordance with another preferred embodiment of the invention.

DETAILED DESCRIPTION OF THE PREFERRED EMBODIMENTS

Figure 2A:
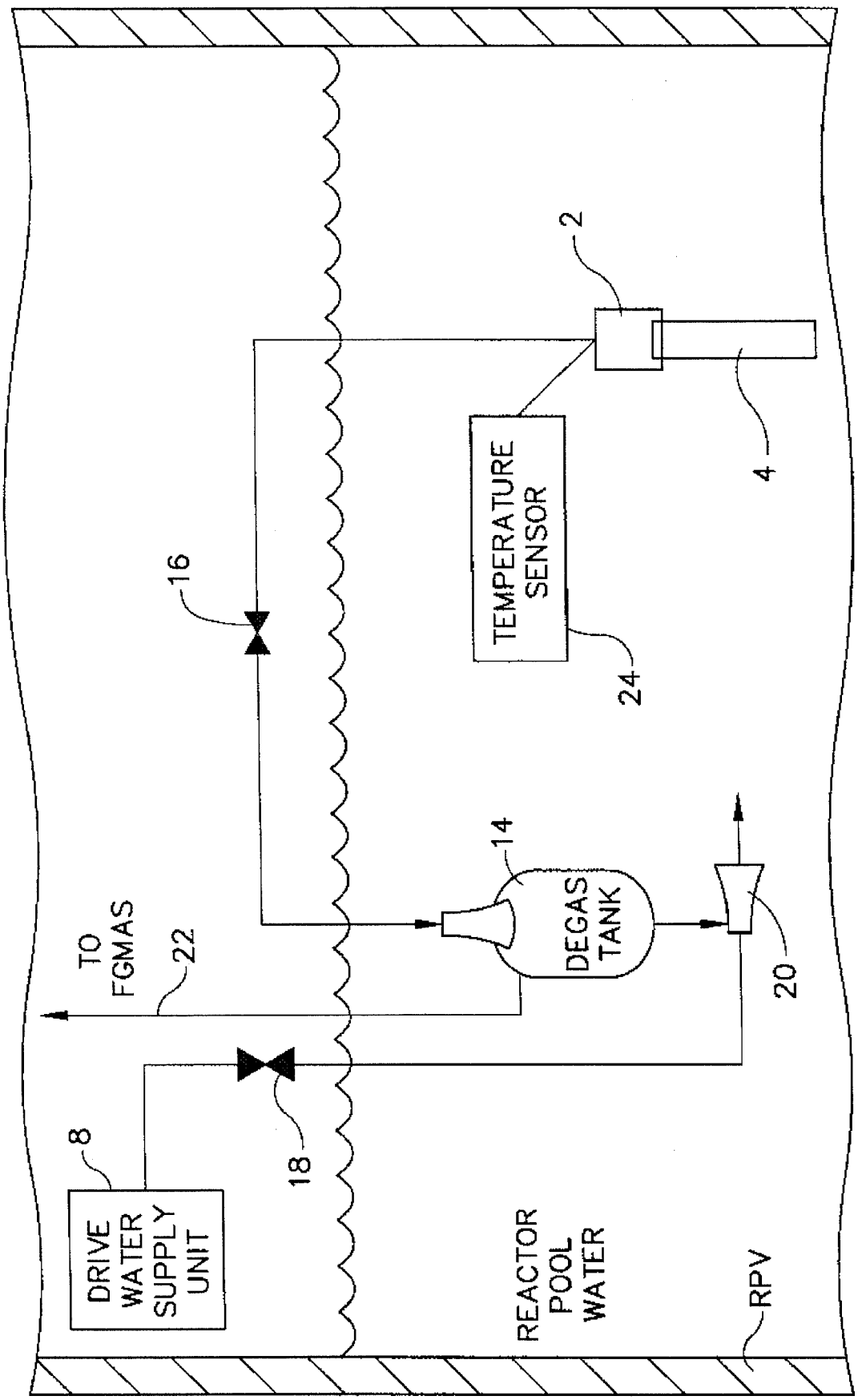
FIGS. 2A and 2B are flow diagrams showing the details of the gas sipping system outlined in FIG. 1.

The basic system consists of means for obtaining a liquid sample from an in situ fuel assembly, means for degassing the sample, means for separating Kr-85 from the gas, means for counting the Kr-85 and a control device. The purpose of the system is to detect failed fuel in situ by determining the amount of Kr-85 present in the degassed sample and comparing that to the normal background level in the reactor pressure vessel or in the fuel storage pool.

In accordance with the preferred embodiment of the invention as generally depicted in FIG. 1, an in-core sipping hood 2 is provided to retrieve the fluid sample from the fuel assembly 4 inside the reactor pressure vessel (not shown). Although FIG. 1 generally depicts a single-head hood seated atop a single fuel assembly, it should be understood that the present invention encompasses the use of a two-head hood to cover two adjacent fuel assemblies, the use of a four-head hood to cover a 2×2 array of fuel assemblies, or any other hood configuration having a plurality of heads covering a corresponding plurality of fuel assemblies. In general, a four-head hood is used for sampling the fuel in the same controlled cell. A two-head hood and a single-head hood are used for sampling the peripheral fuel assemblies.

The sipping hood covers the fuel to be tested from the top of the fuel assembly. The temperature of the fuel rod and the surrounding coolant will be increased due to restricted flow. Higher fuel pellet temperature will increase the fuel rod internal gas pressure, resulting in a higher than normal gas release from any defective fuel rod in the bundle to the surrounding reactor coolant inside the fuel channel. A temperature sensor mounted on the sipping hood measures the temperature change. After a period of soaking, the water sample from each of the fuel assemblies is transferred to the flow control and degas system 6 for treatment. The drive water supply unit 8 provides the drive water source to the flow control and degas system 6.

Two primary advantages of in-core sipping are that the fluid sample can be retrieved from the fuel assembly without any movement of fuel in the core and multiple (multiplexed) sample acquisition and evaluation can be accommodated. This approach will significantly reduce the total required sipping time for a mid-cycle or forced outage.

The gas supply unit 10 provides bottled clean gas with constant pressure and flow rate to carry the degas sample from the flow control and degas system 6 to the fission gas detectors of the fission gas measurement and analysis system 12. It also provides the purge gas to the fission gas measurement and analysis system 12 for system cleanup and regeneration.

Flow control and degas system 6 is a continuous degassing device with a degas tank maintained at a vacuum during operation. The stripped gas from the influent fluid sample of the tested fuel assembly is accumulated inside the degas tank. To minimize the potential radiation exposure and the possibility for contaminated water spillage on the refueling floor, part of the flow control and degas system 6, including the degas tank, is submerged and operated in the reactor pool or fuel storage pool.

At the very beginning and also after completion of the degassing process, the fission gas measurement and analysis system 12 will receive a gas sample from the degas tank for measurement of the Kr-85 content. The fission gas measurement and analysis system 12 separates the Kr-85 from the sample gas and then measures its activity level with a radiation (beta) detector/counter.

In accordance with the invention, a programmable logic controller (PLC) performs system control. It also provides the data acquisition and analysis function for the system. A computer terminal has a touch screen display, a printer/plotter and a tape backup drive. The touch screen monitor is used as the operator interface to the system. It displays the system operation data and screen manual for selection. The printer/plotter provides a hard copy of the test result from each test. A digital analog tape deck records the test data with a removable tape.

The flow control and degas system 6 is mounted on the inside edge of the reactor pressure vessel or reactor pool and the drive water supply unit 8 and the fission gas measurement and analysis system 12 are mounted on the refueling floor near to the flow control and degas system 6. The system controller is set up in a non-contaminated area on the refueling floor. This arrangement and the lines run between units should not interfere with the operation of the refueling platform and auxiliary platform for sipping hood maneuver and with fuel handling from the reactor to the fuel storage pool.

The flow connections for the flow control and degas system 6 of a single detection channel are shown in FIG. 2A. The sipping head 2 covers the fuel to be tested from the top of the fuel assembly 4. A thermocouple 24 mounted inside the sipping hood 2 measures the subsequent temperature increase. After a period of soaking, the water sample from the fuel assembly 4 is transferred to the flow control and degas system 6 for treatment. The flow control and degas system 6 comprises a degas tank 14 having a fluid inlet connectable to sipping hood 2 by means of an open air-operated valve 16, hereinafter referred to as the influent flow shutoff valve. The degas tank has a nozzle connected to an ejector 20, which is driven by water supplied by the drive water supply unit 8 via an open solenoid-actuated valve 18, hereinafter referred to as the drive water supply valve. When the valve (not shown) inside the degas tank nozzle and valves 16 and 18 are open, the ejector 20 draws a vacuum to the degas tank, which vacuum induces the fluid sample to flow from the sipping hood into the degas tank. The stripped gas from the influent fluid sample is initially drawn in for a quick sample and, as the process continues, is accumulated inside the degas tank and later drawn to the fission gas measurement and analysis system via flowline 22.

Figure 2B:
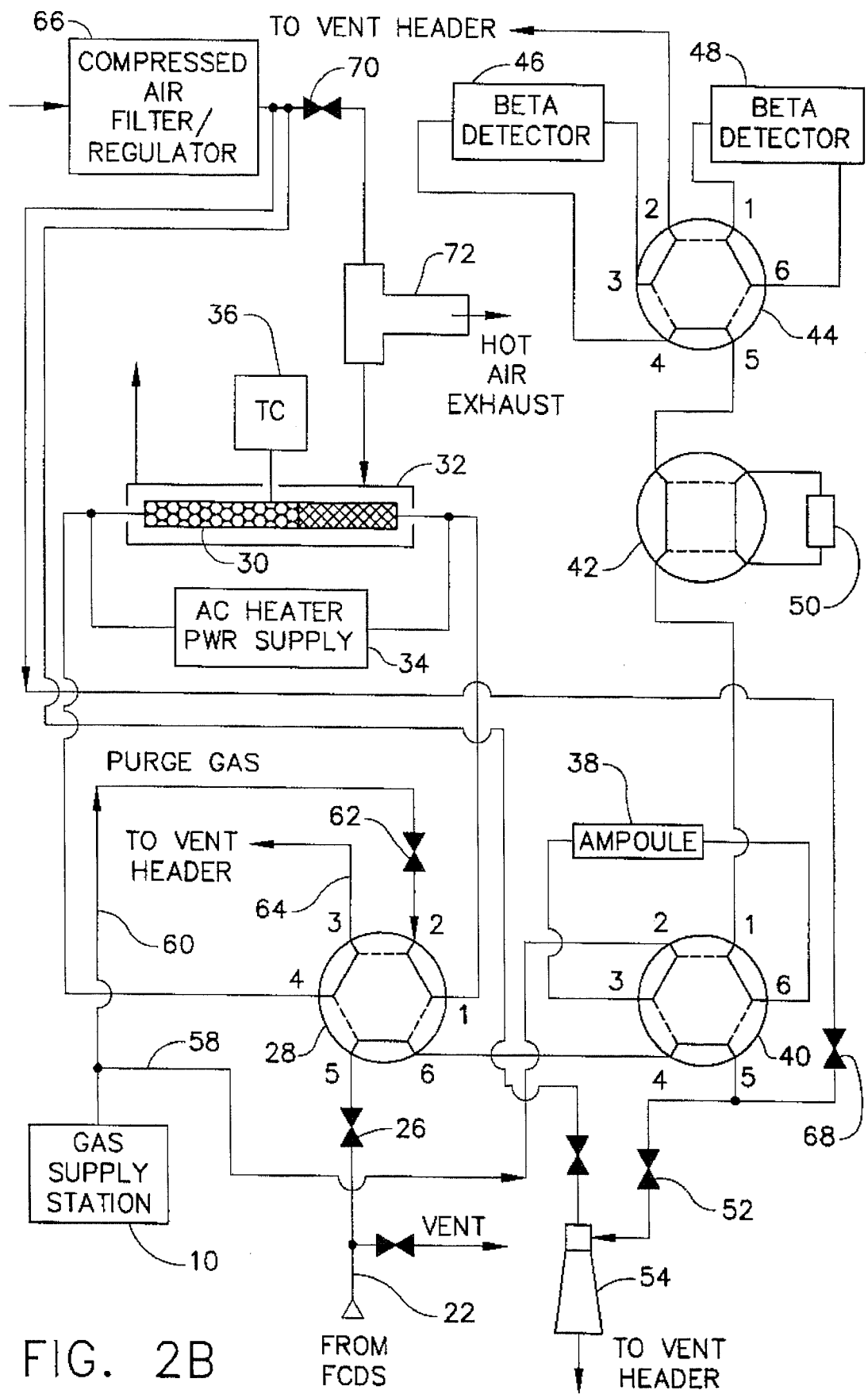

Referring to FIG. 2B, flowline 22 carries the gas sample from the flow control and degas system 6 to the fission gas measurement and analysis system 12. The gas sample flows through a solenoid-actuated valve 26 and enters a first six-way crossover valve 28, which routes the gas sample to a moisture/separation column 30. Column 30 is surrounded by a cooling jacket 32 and has a heater supplied by an ac heater power supply 34. A thermocouple (TC) 36 detects the temperature inside the column. The moisture/separation column 30 contains two packings: a first packing which absorbs moisture and a second packing which absorbs xenon gas but passes krypton gas. With xenon separated out, the gas sample exiting the column is drawn to an ampoule 38 via the first six-way crossover valve 28 and a second six-way crossover valve 40. The separated gas sample is drawn into the ampoule by opening a vacuum valve 52 and turning on a vacuum pump 54. The separated gas sample is held in the ampoule until the time for detection of beta activity. The separated gas sample is then routed to a beta detector 46 via the second six-way crossover valve 40, a four-way crossover valve 42 and a third six-way crossover valve 44. A backup beta detector 48 is also connected to the third six-way crossover valve 44. The gas sample is detected during flow through the beta detector 46 and then vented to the vent header via six-way crossover valve 44. Any beta activity detected as the pressurized gas sample passes through the beta detector indicates the presence of krypton. Beta activity at a level in excess of the background level indicates a leaking fuel rod in the tested fuel assembly. In an alarmed condition, the gas flow will be rerouted to a Kr/Xe separation column 50 for confirmation.

The gas sample in the ampoule 38 is transported to the beta detector by an inert carrier gas, e.g., nitrogen. The carrier gas is supplied from the gas supply station 10 via flowline 58. At the same time the separation column 30 can be backflushed with inert gas via flowline 60, column purge valve 62 and six-way crossover valve 28. The heater is turned on to raise the temperature of the xenon-adsorbing packing to a level whereat the xenon is desorbed. Then the column is purged using nitrogen. The backflushed gas is then routed to the vent header via flowline 64.

Compressed air is used to charge the ampoule 38 via a filter regulator 66 and a purge valve 68. The compressed air, supplied via purge gas supply valve 70, is also used to cool the column jacket 32 after backflushing of the separation column has been completed. Heat is removed from the compressed air via a hot air exhaust 72. The regenerated separation column is thus ready for the next channel cycle.

The drive water could be injected into the bundle for the purpose of backflushing the fuel bundle. Drive water can also be used to flush the fuel sipping hood while moving the hood from one location to another.

The beta detector 46 measures the number of beta particles emitted by the gas sample flowing therethrough and outputs the data electronically. A conventional chart recorder provides a written record of activity levels determined by the beta detector.

All of the valves depicted in FIGS. 2A and 2B, in accordance with the present invention, are operated using solenoids which are controlled by digital outputs from a programmable logic controller (not shown). This enables the detection cycle to be carried out automatically under the control of a computer program.

Figure 4:
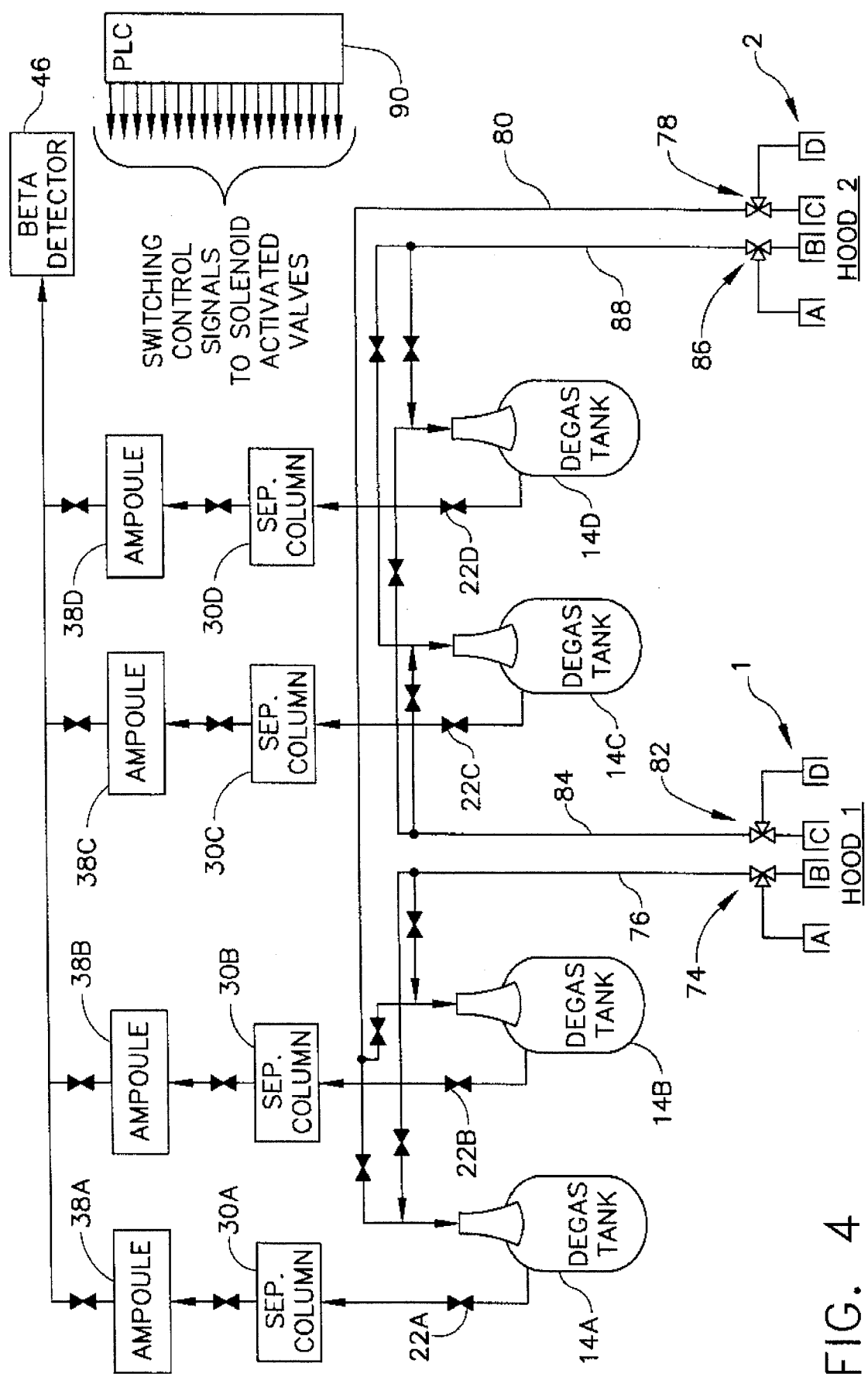
FIG. 4 is a flow diagram showing a multi-channel gas sipping system for detecting leaks in a plurality of fuel assemblies in accordance with yet another preferred embodiment of the invention.

In accordance with the preferred mode of practicing the present invention, a multiplicity of detection channels are incorporated in the system in order to shorten the duration of a gas sipping campaign. Each channel will have the identical hardware shown in FIGS. 2A and 2B. For example, to improve efficiency, four detection channels can be connected in parallel as shown in FIG. 4. These channels are multiplexed in a manner that allows a single beta detector to process the gas samples from all channels in sequence. For ease of discussion, the system shown in FIG. 4 has been simplified to show only two four-head hoods 1 and 2 each having heads A–D; four channels A–D; and a single beta detector 46. Each channel comprises a degas tank (14A–14D), a moisture/separation column (SC) (30A–30D) and a gas sample ampoule (38A–38D) connected in series.

In accordance with this preferred embodiment, each degas tank is coupled to receive a first fluid sample from a respective head of one hood during a first cycle and then receive a second fluid sample from a respective head of the other hood during a second cycle. For example, degas tank 14A (as well as degas tank 14B) can receive a flow sample from either head A or head B of sipping hood 1 via a sample valve 74 for bundle selection at hood 1 and a flowline 76 or from either head C or head D of sipping hood 2 via a sample valve 78 for bundle selection at hood 2 and a flowline 80; and degas tank 14C (as well as degas tank 14D) can receive a flow sample from either head C or head D of sipping hood 1 via a sample valve 82 for bundle selection at hood 1 and a flowline 84 or from either head A or head B of sipping hood 2 via a sample valve 86 for bundle selection at hood 2 and a flowline 88.

Moreover, the cycles for each respective channel are out of phase to allow the four channels to output their respective separated gas samples to the beta detector at different times. The processing of the gas samples in the respective channels is multiplexed in accordance with a predetermined algorithm. Thus,, while one degas tank is receiving an inflowing fluid sample from one sipping hood, another degas tank can be sending an outflowing gas sample, originated in a different sipping hood, to its associated moisture/separation column. Further, while one separated gas sample is being detected in the beta detector 46, other separated gas samples can be held in their respective ampoules. The sequencing of the various process steps is controlled by remote switching of the valves symbolically depicted in FIG. 4. All of these valves are of the solenoid-actuated variety and can be controlled by digital outputs from a programmable logic controller 90 to the solenoids. In addition, it should be noted that although FIG. 4 depicts separate solenoid-actuated valves at the input and output of each ampoule, in accordance with the preferred embodiment of FIG. 2B, both of these valves form part of the six-way crossover valve 40. All valves spring return to close upon loss of power or controls.

In aid of understanding the invention, a general overview of the arrangement and operation of the failed fuel detection system in accordance with the preferred embodiment is given without reference to the drawings. First, a television camera and an illumination device are set up inside the reactor to monitor the in-core sipping activity. The overhead crane and the refueling platform are required to be operable to support the sipping activity. The following plant facilities near the reactor pool area are operable to support fuel sipping: 110 psig instrument-grade compressed air supply; 480/120 electrical power source; 30 gpm, 80 psig pressure demineralized drive water supply; and compressed nitrogen gas cylinders with pressure regulator and flow control valves to provide carrier gas and purge gas for system operation.

Each sipping hood is lowered near to the assigned controlled cell area using a fuel grapple (for moving the heads around) or a general-purpose grapple (for initial installation). Then a system checkup is performed and the pool water background signal level is measured. Then the sipping hoods are moved and mounted on top of the assigned fuel assemblies. The resulting restriction of the flow of coolant through the fuel channel causes the temperature inside the fuel assembly to rise. The fuel in a given fuel assembly is soaked completely with reference to the temperature rise in the respective sipping head.

The remainder of the procedure will be described with reference to a single channel for the sake of convenience. First, the degas tank is fully filled with reactor pool water. A small quantity of gas is injected into the degas tank to clear a space at the top. Then drawing vacuum of the degas tank is started. When the tank pressure reaches a preset point, the influent flow shutoff valve from the selected fuel assembly is opened and gas stripping of the fluid sample is started. While gas stripping is ongoing, a higher vacuum is drawn to the ampoule relative to the degas tank. Then a quick sample is drawn from the degas tank to the ampoule. The degassing process is terminated if a gross leaker is identified upon analysis of the quick sample. If no gross leaker is identified, the separation column is cleaned by back purging of the gas sampling flow path. Then a high vacuum is drawn to the column. Upon completion of gas stripping of the fluid sample, the vacuum pump is stopped and the degas tank is filled with reactor pool water to compress the gas sample contained in the degas tank. Then the final gas sample is drawn from the degas tank and sent to the fission gas measurement and analysis system for processing. The gas sample is separated to remove moisture and xenon; then the separated gas sample is sent to the beta detector for measurement. In an alarmed condition, the gas flow is rerouted to a Kr/Xe separation column for confirmation. The collected gas samples in the other ampoules are held in place until the system is ready again for automatic operation. After each cycle, the separation column must be regenerated. Upon completion of testing of gas samples from all four fuel assemblies of a fuel cell, the sipping hood is moved to the next assigned location for testing.

In accordance with a further aspect of the invention, gas sipping can be performed while the fuel assembly 4 is being carried on the refueling mast 100, as depicted in FIG. 3. The refueling mast has a grapple 102 on which the bail 104 of the fuel assembly is hooked. A sipping hood 106 is mounted on the refueling mast and is designed to fit over the top of the fuel assembly suspended from the grapple 102. Annular sealing means 110 prevent the escape of gas from the chamber under the hood. The hood has inlet and outlet flowlines which terminate in couplings 108 and 108' for connection to the flow control and degas system disclosed hereinabove.

The preferred embodiment of the invention has been disclosed for the purpose of illustration. Variations and modifications of the disclosed structure which do not depart from the concept of this invention will be readily apparent to engineers skilled in the art of gas processing. All such variations and modifications are intended to be encompassed by the claims set forth hereinafter.

What is claimed is:

1. A system for detecting a defective fuel rod in a fuel assembly, comprising:

a sipping hood which fits on top of said fuel assembly;

means for accumulating a gas sample from fluid trapped under said sipping hood; and means for detecting the presence of krypton in said gas sample.

2. The system as defined in claim 1, wherein said gas accumulating means comprises a degas tank connected to receive a fluid sample from said sipping hood.

3. The system as defined in claim 2, wherein said degas tank has a nozzle, further comprising an ejector coupled to said nozzle for drawing vacuum in said degas tank.

4. The system as defined in claim 1, wherein said krypton detecting means comprises a separation column containing material for adsorbing xenon and passing krypton in a gas sample flowing through said separation column, and a beta detector for detecting the beta activity in said gas sample after removal of xenon by said separation column.

5. The system as defined in claim 4, wherein said separation column contains material for adsorbing moisture in a gas sample flowing through said separation column, said moisture-adsorbing material being placed upstream of said xenon-adsorbing material.

6. The system as defined in claim 5, further comprising means for heating said separation column and means for cooling said separation column.

7. The system as defined in claim 4, wherein said krypton detecting means further comprises an ampoule for receiving said gas sample from said separation column and holding said gas sample until said gas sample is to be routed to said beta detector.

8. The system as defined in claim 1, wherein a temperature sensor is mounted inside said sipping hood.

9. The system as defined in claim 1, wherein said sipping hood is carried on a refueling mast.

10. A gas sipping hood for positioning on top of a fuel assembly comprising:

means for defining a chamber above said fuel assembly;

means for preventing escape of fluid from said chamber; and valve means for releasing a fluid sample from said chamber.

11. The gas sipping hood as defined in claim 10, wherein a temperature sensor is mounted inside said sipping hood for detecting the temperature inside said chamber.

12. A method for detecting a defective fuel rod in a fuel assembly, comprising the steps of:

arranging a hood on top of said fuel assembly;

accumulating a gas sample from fluid trapped under said sipping hood; and detecting for the presence of krypton in said gas sample.

13. The method as defined in claim 12, wherein said fuel assembly is located inside the core of a nuclear reactor.

14. The method as defined in claim 12, wherein said fuel assembly is suspended from a refueling mast.

15. The method as defined in claim 12, wherein said detecting step comprises the steps of separating xenon from said gas sample and then detecting the level of beta activity in said gas sample without xenon.

16. The method as defined in claim 15, wherein said detecting step comprises the steps of detecting the level of beta activity in a sample of reactor pool water and comparing the level of beta activity in said reactor pool water sample with the level of beta activity in said gas sample without xenon.

17. The method as defined in claim 12, wherein said step of accumulating a gas sample comprises the step of drawing a vacuum across a submerged nozzle of a degas tank connected to said hood.

18. A system for detecting a defective fuel rod in first and second fuel assemblies, comprising:

first and second sipping hood means arranged on top of said first and second fuel assemblies respectively;

first and second bundle selection valve means respectively coupled to said first and second sipping hood means;

means for detecting the level of beta activity in a gas sample;

first and second gas sample valve means respectively coupled to said beta activity level detecting means;

first and second channels having respective inlets selectively coupled to said first and second sipping hood means by said first and second bundle selection valve means respectively, and having respective outlets selectively coupled at different times to said beta activity level detecting means by said first and second gas sample valve means respectively; and programmable logic control means coupled to said first and second bundle selection valve means and to said first and second gas sample valve means for controlling said valve means to multiplex respective gas samples from said first and second sipping hoods through said first and second channels respectively.

19. The system as defined in claim 18, wherein said first channel comprises a first degas tank connected to receive a fluid sample from said first sipping hood and said second channel comprises a second degas tank connected to receive a fluid sample from said second sipping hood.

20. The system as defined in claim 19, wherein said first channel comprises a first separation column connected to receive a gas sample from said first degas tank and said second channel comprises a second separation column connected to receive a gas sample from said second degas tank, both of said first and second separation columns being packed with material which adsorbs xenon but does not adsorb krypton when a gas sample containing both xenon and krypton passes therethrough.

* * * * *